(12) United States Patent
Schur et al.

(10) Patent No.: US 9,737,330 B2
(45) Date of Patent: *Aug. 22, 2017

(54) CUTTING WIRE ASSEMBLY FOR USE WITH A CATHETER

(71) Applicants: Israel Schur, Teaneck, NJ (US); Rex Medical, L.P., Conshohocken, PA (US)

(72) Inventors: Israel Schur, Teaneck, NJ (US); James F. McGuckin, Jr., Radnor, PA (US); James Erich Bressler, Langhorne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,681

(22) Filed: Sep. 4, 2015

(65) Prior Publication Data

US 2015/0374403 A1    Dec. 31, 2015

Related U.S. Application Data

(60) Continuation of application No. 14/181,658, filed on Feb. 15, 2014, now abandoned, which is a division of
(Continued)

(51) Int. Cl.
*A61B 17/22* (2006.01)
*A61B 17/3207* (2006.01)
*A61M 25/10* (2013.01)

(52) U.S. Cl.
CPC ............ *A61B 17/32075* (2013.01); *A61B 17/320725* (2013.01); *A61M 25/104* (2013.01);
(Continued)

(58) Field of Classification Search
CPC ...... A61M 25/00; A61M 25/10; A61M 29/00; A61B 17/32; A61B 17/3207;
(Continued)

(56) References Cited

U.S. PATENT DOCUMENTS 5,158,564 A    10/1992  Schnepp-pesch
5,176,693 A    1/1993   Pannek, Jr.
(Continued)

FOREIGN PATENT DOCUMENTS

WO    WO-98/19608      5/1998
WO    WO-2004/041329   5/2004
(Continued)

OTHER PUBLICATIONS

EP-11 18 3669—European Search Report. Date of completion of the search, Jan. 23, 2012.

*Primary Examiner* — Ashley Fishback
(74) *Attorney, Agent, or Firm* — Neil D. Gershon

(57) ABSTRACT

A method of treating a lesion in a body lumen to enlarge a passageway in the lumen including providing a cutting member, connecting a tracking member to the cutting member to form an assembly, inserting the connected cutting member and tracking member through a first lumen of a catheter, withdrawing the catheter from the cutting member and tracking member, inserting the catheter over the tracking member and leaving the cutting member outside the catheter, and expanding a portion of the catheter to move the cutting member into cutting contact with the lesion. A device for treating a lesion in a body lumen including a cutting member having a coupler to connect a tracking member is also provided.

19 Claims, 4 Drawing Sheets

Related U.S. Application Data application No. 13/226,708, filed on Sep. 7, 2011, now Pat. No. 8,702,736.

(60) Provisional application No. 61/415,883, filed on Nov. 22, 2010.

(52) U.S. Cl.
CPC ............ *A61B 2017/22038* (2013.01); *A61B 2017/22045* (2013.01); *A61B 2017/22061* (2013.01); *A61B 2017/320733* (2013.01); *A61B 2017/320741* (2013.01)

(58) Field of Classification Search
CPC .. A61B 17/320725; A61B 2017/22001; A61B 2017/22038; A61B 2017/22051
See application file for complete search history.

(56) References Cited

U.S. PATENT DOCUMENTS

| | | |
|---|---|---|
| 5,196,024 A | 3/1993 | Barath |
| 5,211,651 A | 5/1993 | Reger |
| 5,282,484 A | 2/1994 | Reger |
| 5,320,634 A | 6/1994 | Vigil |
| 5,431,673 A | 7/1995 | Summers |
| 5,527,326 A | 6/1996 | Hermann |
| 5,549,552 A | 8/1996 | Peters et al. |
| 5,554,163 A | 9/1996 | Shturman |
| 5,556,408 A | 9/1996 | Farhat |
| 5,616,149 A | 4/1997 | Barath |
| 5,628,746 A | 5/1997 | Clayman |
| 5,658,301 A | 8/1997 | Lemaitre |
| 5,665,098 A | 9/1997 | Kelly |
| 5,697,944 A | 12/1997 | Lary |
| 5,728,123 A | 3/1998 | Lemelson |
| 5,772,676 A | 6/1998 | Cuschieri |
| 5,797,935 A | 8/1998 | Barath |
| 5,897,567 A | 4/1999 | Ressemann |
| 5,904,679 A | 5/1999 | Clayman |
| 5,941,869 A | 8/1999 | Patterson |
| 6,022,362 A | 2/2000 | Lee |
| 6,027,514 A | 2/2000 | Stine |
| 6,036,708 A | 3/2000 | Sciver |
| 6,156,043 A | 12/2000 | Krahn |
| 6,165,187 A | 12/2000 | Reger |
| 6,165,195 A | 12/2000 | Wilson |
| 6,210,380 B1 | 4/2001 | Mauch |
| 6,221,090 B1 | 4/2001 | Wilson |
| 6,264,667 B1 | 7/2001 | McGuckin, Jr. |
| 6,361,544 B1 | 3/2002 | Wilson |
| 6,387,108 B1 | 5/2002 | Taylor |
| 6,394,995 B1 | 5/2002 | Solar |
| 6,440,147 B1 | 8/2002 | Lee |
| 6,447,501 B1 | 9/2002 | Solar |
| 6,475,222 B1 | 11/2002 | Berg |
| 6,494,875 B1 | 12/2002 | Mauch |
| 6,508,836 B2 | 1/2003 | Wilson |
| 6,565,588 B1 | 5/2003 | Clement |
| 6,632,231 B2 | 10/2003 | Radisch, Jr. |
| 6,702,831 B2 | 3/2004 | Lee |
| 6,740,104 B1 | 5/2004 | Solar |
| 6,746,463 B1 | 6/2004 | Schwartz |
| 6,780,174 B2 | 8/2004 | Mauch |
| 6,780,179 B2 | 8/2004 | Lee |
| 6,780,199 B2 | 8/2004 | Solar |
| 6,796,989 B2 | 9/2004 | Uflacker |
| 6,808,531 B2 | 10/2004 | Lafontaine |
| 6,824,551 B2 | 11/2004 | Trerotola |
| 6,835,059 B2 | 12/2004 | Skinner |
| 6,872,204 B2 | 3/2005 | Houser |
| 6,942,680 B2 | 9/2005 | Grayzel |
| 6,951,566 B2 | 10/2005 | Lary |
| 7,008,434 B2 | 3/2006 | Kurz |
| 7,008,438 B2 | 3/2006 | O'Brien |
| 7,029,450 B2 | 4/2006 | Gellman |
| 7,070,576 B2 | 7/2006 | O'Brien |
| 7,131,981 B2 | 11/2006 | Appling et al. |
| 7,147,631 B2 | 12/2006 | Scopton |
| 7,153,315 B2 | 12/2006 | Miller |
| 7,172,609 B2 | 2/2007 | Radisch, Jr. |
| 7,179,024 B2 | 2/2007 | Greenhalgh |
| 7,252,674 B2 | 8/2007 | Wyzgala |
| 7,270,673 B2 | 9/2007 | Yee |
| 7,279,002 B2 | 10/2007 | Shaw |
| 7,291,158 B2 | 11/2007 | Crow |
| 7,294,117 B2 | 11/2007 | Provost-tine |
| 7,303,572 B2 | 12/2007 | Melsheimer |
| 7,329,267 B2 | 2/2008 | Weber |
| 7,344,546 B2 | 3/2008 | Wulfman |
| 7,396,358 B2 | 7/2008 | Appling |
| 7,399,307 B2 | 7/2008 | Evans |
| 7,416,555 B2 | 8/2008 | Krivoruchko |
| 7,479,153 B2 | 1/2009 | Belef |
| 7,494,497 B2 | 2/2009 | Weber |
| 7,517,352 B2 | 4/2009 | Evans |
| 7,632,288 B2 | 12/2009 | Wu |
| 7,637,885 B2 | 12/2009 | Maschke |
| 7,648,502 B2 | 1/2010 | Jacques |
| 7,658,744 B2 | 2/2010 | Jackson |
| 7,662,163 B2 | 2/2010 | Grayzel |
| 7,691,116 B2 | 4/2010 | Goodin |
| 7,734,332 B2 | 6/2010 | Sher |
| 7,736,375 B2 | 6/2010 | Crow |
| 7,753,907 B2 | 7/2010 | Dimatteo |
| 7,754,047 B2 | 7/2010 | Kelley |
| 7,758,604 B2 | 7/2010 | Wu |
| 7,771,447 B2 | 8/2010 | Kunis |
| 7,780,626 B2 | 8/2010 | Wu |
| 7,799,043 B2 | 9/2010 | O'Brien |
| 7,833,223 B2 | 11/2010 | Vakharia |
| 7,862,575 B2 | 1/2011 | Tal |
| 7,883,537 B2 | 2/2011 | Grayzel |
| 7,887,557 B2 | 2/2011 | Kelley |
| 7,901,378 B2 | 3/2011 | Solar |
| 7,919,910 B2 | 4/2011 | Eidenschink |
| 7,955,350 B2 | 6/2011 | Konstantino |
| 7,985,234 B2 | 7/2011 | Wang |
| 8,070,729 B2 | 12/2011 | Solar |
| 8,080,026 B2 | 12/2011 | Konstantino |
| 8,348,987 B2 | 1/2013 | Eaton |
| 2003/0055444 A1 | 3/2003 | Evans |
| 2003/0163148 A1 | 8/2003 | Wang |
| 2003/0195546 A1 | 10/2003 | Solar |
| 2003/0208219 A1* | 11/2003 | Aznoian .......... A61B 17/32056 606/170 |
| 2004/0087876 A1 | 5/2004 | Eskuri |
| 2004/0122458 A1 | 6/2004 | Opie |
| 2004/0133148 A1* | 7/2004 | Jacques ............ A61B 17/32056 604/22 |
| 2004/0193196 A1 | 9/2004 | Appling et al. |
| 2004/0199088 A1 | 10/2004 | Bakos |
| 2005/0085836 A1 | 4/2005 | Raymond |
| 2005/0119678 A1 | 6/2005 | O'Brien |
| 2005/0137615 A1 | 6/2005 | Mapes |
| 2005/0197593 A1 | 9/2005 | Burbank |
| 2005/0209617 A1 | 9/2005 | Koven |
| 2005/0240144 A1 | 10/2005 | Cheves |
| 2005/0288629 A1 | 12/2005 | Kunis |
| 2006/0085026 A1* | 4/2006 | Appling .......... A61B 17/32072 606/194 |
| 2006/0111736 A1 | 5/2006 | Kelley |
| 2006/0116700 A1 | 6/2006 | Crow |
| 2006/0116701 A1 | 6/2006 | Crow |
| 2006/0178685 A1 | 8/2006 | Melsheimer |
| 2006/0206125 A1 | 9/2006 | Fogarty |
| 2007/0016232 A1 | 1/2007 | St. Martin |
| 2007/0233163 A1 | 10/2007 | Bombard |
| 2007/0250096 A1 | 10/2007 | Yamane |
| 2007/0270893 A1 | 11/2007 | Pikus |
| 2008/0045987 A1 | 2/2008 | Lee |
| 2008/0077164 A1 | 3/2008 | Murphy |
| 2008/0077165 A1 | 3/2008 | Murphy |
| 2008/0147103 A1 | 6/2008 | Shekalim |

(56) References Cited

U.S. PATENT DOCUMENTS

| | | |
|---|---|---|
| 2008/0215077 A1 | 9/2008 | Sepetka |
| 2008/0228208 A1 | 9/2008 | Wulfman |
| 2008/0249552 A1 | 10/2008 | Eliachar |
| 2008/0255595 A1 | 10/2008 | Buchbinder |
| 2008/0255596 A1 | 10/2008 | Jenson |
| 2008/0269789 A1 | 10/2008 | Eli |
| 2008/0306499 A1 | 12/2008 | Katoh |
| 2009/0012548 A1 | 1/2009 | Thatcher |
| 2009/0099581 A1 | 4/2009 | Kim |
| 2009/0105686 A1 | 4/2009 | Snow |
| 2009/0125044 A1 | 5/2009 | Lary |
| 2009/0306582 A1 | 12/2009 | Granada |
| 2010/0010521 A1 | 1/2010 | Kurrus |
| 2010/0023035 A1 | 1/2010 | Kontos |
| 2010/0057077 A1 | 3/2010 | Ducharme |
| 2010/0094259 A1 | 4/2010 | Makower |
| 2010/0094320 A1 | 4/2010 | Arat |
| 2010/0121361 A1 | 5/2010 | Plowe |
| 2010/0125266 A1 | 5/2010 | Deem |
| 2010/0137893 A1 | 6/2010 | Kilemnick |
| 2010/0198191 A1 | 8/2010 | Clifford |
| 2010/0234864 A1 | 9/2010 | Keller |
| 2010/0286720 A1 | 11/2010 | Shaked |
| 2011/0034949 A1 | 2/2011 | Solar |
| 2011/0071559 A1 | 3/2011 | Holman |
| 2011/0087257 A1 | 4/2011 | To |
| 2011/0118774 A1 | 5/2011 | Solar |
| 2011/0125132 A1 | 5/2011 | Krolik et al. |
| 2011/0125172 A1 | 5/2011 | Gelbart |
| 2011/0160645 A1 | 6/2011 | Sutermeister et al. |

FOREIGN PATENT DOCUMENTS

| | | |
|---|---|---|
| WO | WO-2010/002549 | 1/2010 |
| WO | WO-2010/003135 | 1/2010 |
| WO | WO-2010/011956 | 1/2010 |

\* cited by examiner

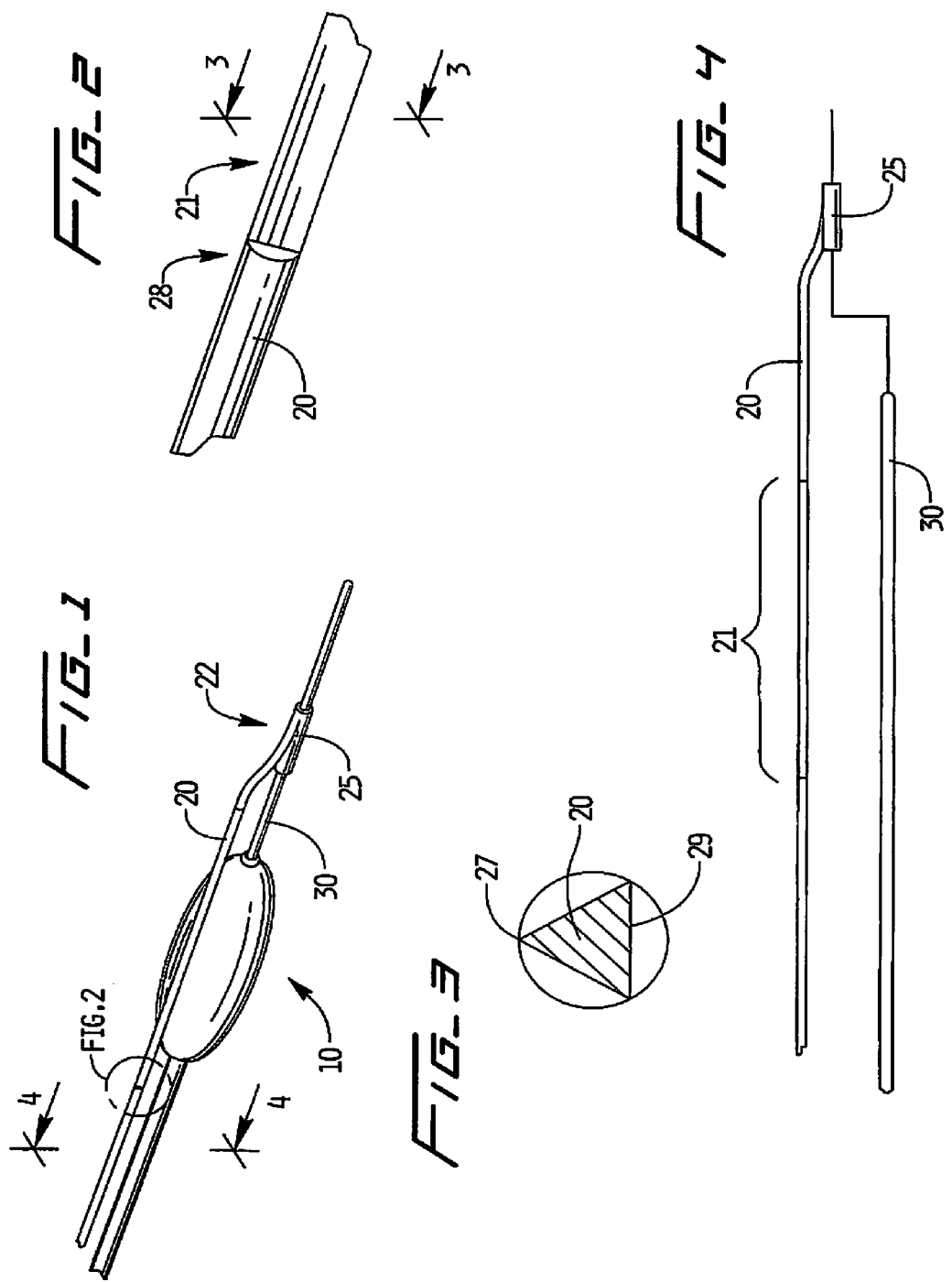

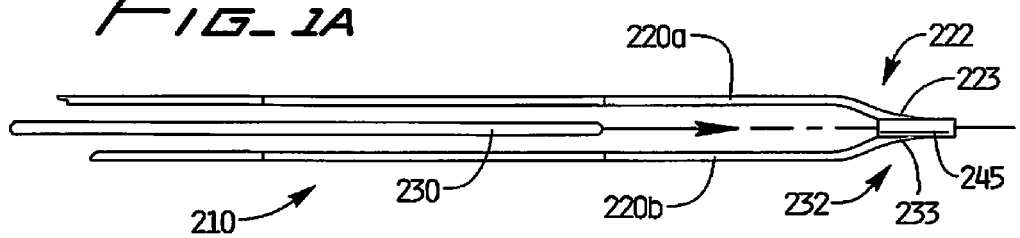
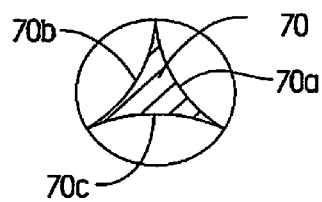 
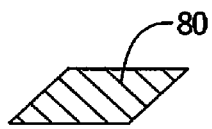 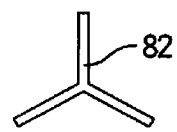 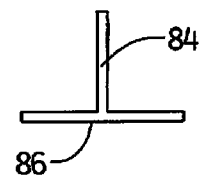
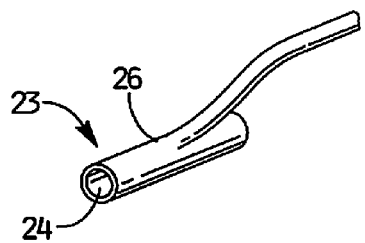 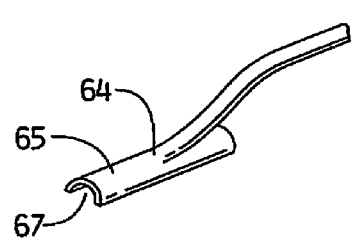

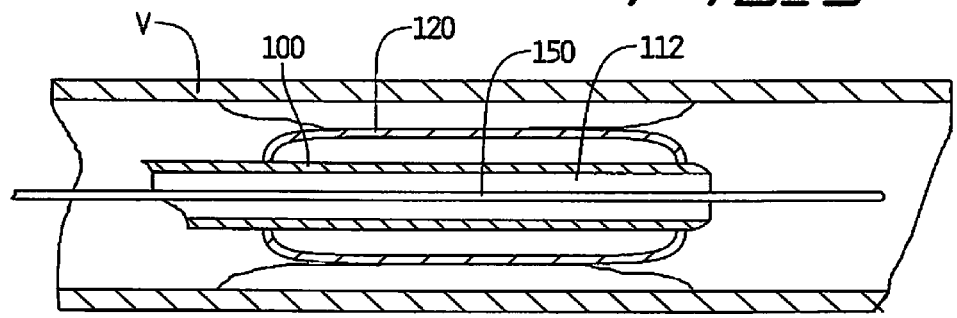
FIG_5
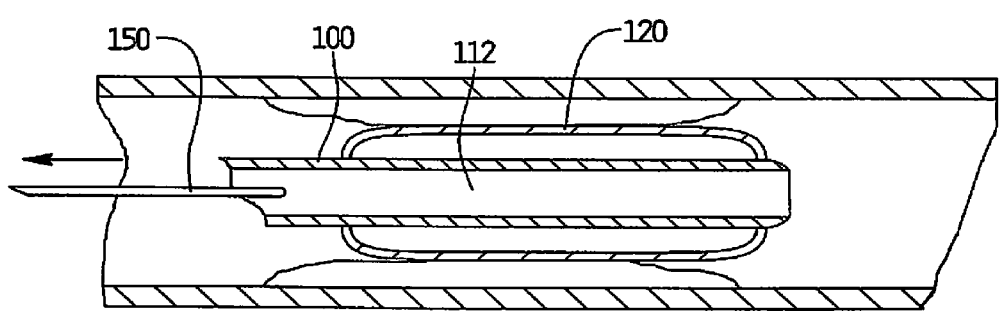
FIG_5A
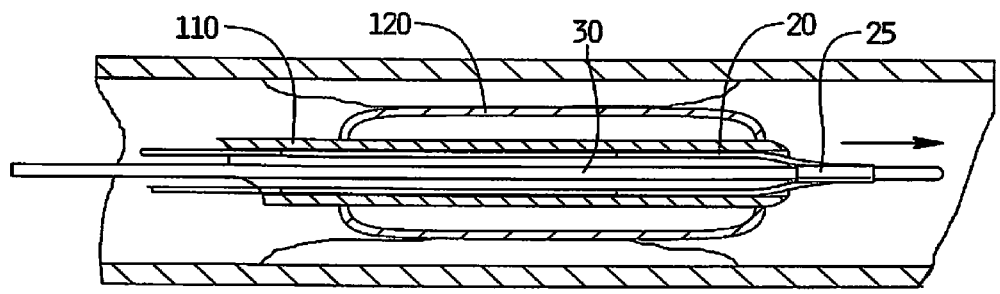
FIG_5B

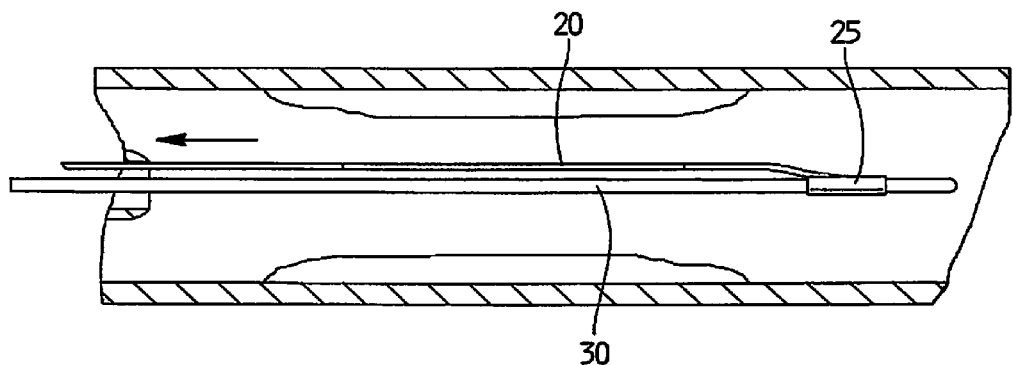
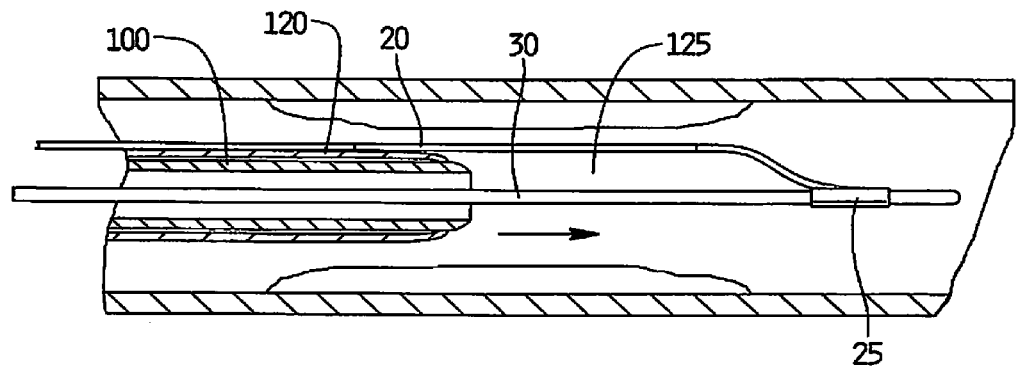
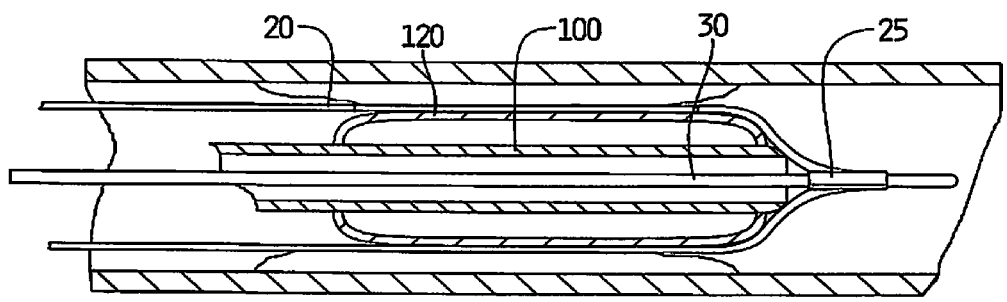

CUTTING WIRE ASSEMBLY FOR USE WITH A CATHETER

This application is a continuation of U.S. application Ser. No. 14/181,658, filed Feb. 15, 2013, which is a divisional of U.S. application Ser. No. 13/226,708, filed Sep. 7, 2011, which claims priority from provisional application Ser. No. 61/415,883, filed Nov. 22, 2010. The entire contents of each of these applications are incorporated herein by reference.

BACKGROUND

Technical Field

This application relates to a method for treating stenotic lesions of a vessel and more particularly relates to a cutting wire for use with a catheter to open stenotic lesions in vessels.

Background of Related Art

Several methods have been utilized to treat stenotic lesions of vessels. With stenotic lesions, the vessel diameter is constricted and therefore attempts have been made to widen this constriction. One method is an invasive surgical procedure where the vessel wall is cut open and the portion containing the plaque or other constricting structure is removed. This procedure is traumatic, complex, and results in a long recovery time for the patient. It also causes a weakening of the vessel wall since a portion of the wall is removed. A weakened wall can ultimately result in an aneurysm which is a dilatation (expansion) of the artery, which adversely affects vessel function and if not surgically treated could be life threatening to the patient.

In order to reduce trauma to the patient, reduce the patient recovery time and reduce hospital costs, minimally invasive procedures have been developed to treat stenotic lesions. Balloon angioplasty is one such method. In angioplasty, a balloon is placed in the stenosed (restricted) portion of the vessel and inflated to compress the plaque against the vessel wall, thereby increasing the lumen in the vessel to improve blood flow. That is, the balloon is inflated to push the lesion radially outwardly to widen the passageway. Some stenotic lesions are resistant to conventional pressure balloons. Consequently, high pressure balloons have been developed to treat resistant stenotic lesions. However, such high pressure balloons apply more force and increase the risk of vessel trauma and rupture. Moreover, sometimes lesions are even resistant to these high pressure balloons.

Additionally, the use of these angioplasty balloon catheters oftentimes have only short term effect as it has been found that restensois frequently occurs after such treatment.

In an attempt to address such drawbacks as reducing the likelihood of restenosis, trauma as well as to treat vessels with highly resistant lesions, cutting balloon catheters were developed. One such device is disclosed for example in U.S. Pat. No. 5,196,024 which describes a catheter with a balloon and longitudinal cutting edges. One of the many disadvantages of this device, however, is it requires modifications of balloon catheters which significantly increases the cost of the catheter. Another disadvantage is that instead of using the procedural catheter, a different catheter may be required with a cutting balloon. Consequently, the surgeon would need to decide prior to the procedure which type of catheter to utilize, although this may not always be practical as the information to determine the type (e.g. resistance) of the lesion may not be available until the lesion is accessed and the extent of the disease is known. Thus, for example, the surgeon may insert an angioplasty catheter, inflate the balloon and find that it is insufficient to widen the vessel passageway. The surgeon would then need to conduct the time consuming task of removing the catheter and inserting a cutting balloon catheter, threading it through the vascular system over a guidewire. Since the catheters are inserted from a remote site, e.g. through the femoral artery, these catheter exchanges take time and increase trauma to the patient. Additionally, it adds to the cost of the procedure since two catheters would be required. In order to properly treat the diverse size and condition of each lesion a large inventory of multiple sized cutting balloons would be required.

Conversely, in certain procedures, utilizing a cutting balloon in soft lesions increases the risk of trauma or damage to the vessel and therefore it would not be desirable to use a cutting balloon catheter. Thus, an exchange for an angioplasty catheter would be necessary.

Such catheter exchanges might also require guidewire exchanges since the standard 0.035" guidewire utilized for an angioplasty catheter may be too large for the 0.018" cutting balloon catheter. The guidewire exchanges complicate the procedure, increase the risk to the patient and increase the procedure time, thereby increasing costs to the patient.

U.S. Pat. No. 7,131,981 attempts to address the foregoing issues by providing a conversion device comprising an insertion tube insertable into the normal 0.035" guidewire lumen of an angioplasty catheter. This device would not work for angioplasty catheters with small guidewire lumens. The tube has two jacket segments and a guide insert device having a channel and four guide channels. Because of the complexity of the device, the cutting elements in the four channels would need to be sufficiently thin to be maintained in the smaller diameter device. Such thin (small diameter) cutting elements however may be too flexible and not have adequate stiffness to be effective. Additionally, the cutting elements are attached at one end, having an opposite free end which can potentially damage and perforate the vessel wall during use.

The need therefore exists for an improved, more simplified device and method to enable the selective use of a cutting wire for treating stenosis.

SUMMARY

The present invention overcomes the disadvantages and deficiencies of the prior art.

In one aspect, the present invention provides a method of treating a lesion in a body lumen comprising providing a cutting member, connecting a tracking member to the cutting member to form an assembly, inserting the connected cutting member and tracking member through a first lumen of a catheter, withdrawing the catheter from the cutting member and tracking member, inserting the catheter over the tracking member while leaving the cutting member outside the catheter, and expanding a portion of the catheter to move the cutting member into cutting contact with the lesion to enlarge a passageway in the body lumen.

In some embodiments, the step of inserting a catheter over the tracking member comprises reinserting the same catheter through which the cutting member and tracking member were initially inserted. In other embodiments, a different catheter is utilized.

The catheter preferably includes an expandable balloon, and the step of expanding a portion of the catheter preferably includes the step of expanding the balloon to cause the cutting member to be moved radially with respect to the catheter. Preferably, the step of expanding a portion of the catheter causes a gap between the cutting member and tracking member to widen.

In some embodiments, the cutting member has a cutting edge opposite an edge facing the tracking member, and expansion of a portion of the catheter forces the cutting edge into a diseased narrowed section within the lesion.

In some embodiments, the length of the tracking member can exceed the length of the cutting member. The cutting member and tracking member can be in the form of wires.

In another aspect, the present invention provides a method of treating a lesion in a body lumen to enlarge a passageway in the body lumen comprising providing a cutting member, connecting a tracking member to the cutting member, inserting the connected cutting member and tracking member into the body lumen, inserting a catheter over the tracking member so the tracking member extends through a first lumen of the catheter and the cutting member does not extend through the first lumen, and moving the cutting member away from the tracking member into cutting contact with the lesion to enlarge the passageway in the body lumen.

Preferably, the step of inserting a cutting member and tracking member comprises the step of inserting the cutting member and tracking member through a lumen of a catheter. In some embodiments, the catheter through which the cutting and tracking members are initially inserted is the same catheter subsequently inserted over the tracking member. In other embodiments, a different catheter is utilized. In some embodiments, the step of moving the cutting member comprises the step of expanding a balloon of the catheter. In preferred embodiments, the cutting member and tracking member are wires inserted as a unit into the body lumen.

In another aspect, the present invention provides a device for treating a lesion in a body lumen to enlarge a passageway in a body lumen comprising a cutting member having a proximal portion, a distal portion and a coupler for coupling a tracking member thereto. The cutting member with coupled tracking member are insertable into the body lumen as a unit, the cutting member configured for movement in a direction transverse to a longitudinal axis of the tracking member to widen a gap between the cutting member and tracking member at least at a distal region.

In some embodiments, the cutting member has a cutting surface on a first surface opposite a second surface facing the tracking member. In one embodiment, the cutting member has a cutting surface with a flat edge on an edge opposite the second surface. The second surface can have a convex surface.

In some embodiments, the cutting member has a cutting surface and an atraumatic surface proximal of the cutting surface.

BRIEF DESCRIPTION OF THE DRAWINGS

Preferred embodiment(s) of the present invention are described herein with reference to the drawings wherein:

FIG. 1 is a perspective view of a conventional balloon catheter and tracking wire for use with the cutting wire of the present invention;

FIG. 1A is a side view of an alternative embodiment of the present invention;

FIG. 2 is a perspective view of the area of detail of FIG. 1 showing a portion of the cutting wire in accordance with one embodiment;

FIG. 3 is a transverse cross-sectional view of the cutting wire taken along lines 3-3 of FIG. 2;

FIGS. 3A-3E are cross-sectional views of alternate embodiments of the cutting wire of the present invention;

FIG. 4 is side view of the cutting wire and tracking wire of FIG. 1 prior to their attachment;

FIG. 4A is a perspective view of the coupler of the cutting wire of FIG. 4;

FIG. 4B is a perspective view of an alternate embodiment of the coupler;

FIGS. 5-5E illustrate the method steps for use of the cutting wire of the present invention, the drawings showing cross-sectional views, wherein FIG. 5 illustrates a conventional balloon catheter inserted over a conventional guidewire;

FIG. 5A illustrates withdrawal of the conventional guidewire;

FIG. 5B illustrates insertion of the of the cutting and tracking members of the present invention through the balloon catheter lumen;

FIG. 5C illustrates withdrawal of the balloon catheter;

FIG. 5D illustrates the balloon catheter inserted over the tracking member; and FIG. 5E illustrates expansion of the balloon of the balloon catheter to force the cutting member into cutting contact with the lesion.

DETAILED DESCRIPTION OF PREFERRED EMBODIMENTS

Referring now in detail to the drawings wherein like reference numerals identify similar or like components throughout the several views, a cutting member of the present invention is disclosed for use with a tracking member. The tracking member is designated generally by reference numeral 30, and is preferably in the form of a wire, and the cutting member is designated generally by reference numeral 20, and is preferably in the form of a wire. As discussed in more detail below, the tracking wire 30 and cutting wire 20 are attached at a distal portion by the user prior to their insertion so they are insertable as a unit, thus forming a cutting assembly 10. The tracking wire 30 can be a specifically designed wire or can be a conventional guidewire so the cutting wire 20 can be used with a conventional guidewire. After attachment of the two components, the assembly 10 can be used with a conventional catheter, such as an angioplasty catheter.

The device of the present invention functions to treat the stenotic lesion inside the vessel wall, thereby opening or enlarging the passageway in the vessel which was restricted. The stenosis can be a result of plaque buildup, endothelial growth, blood clots, etc. The device can also be used to treat other lesions restricting passageways in other body lumens.

With reference to FIGS. 1 and 5C, cutting member in the form of a wire 20 has a distal portion 22 with a coupler 25 extending therefrom. In one embodiment, the coupler 25 is in the form of a collar 26 (FIG. 4A). Coupler 25 can be integral or a separate component attached to wire 20. If a separate component, the user assembles the wires 20 and 30 by attaching the coupler to both the wires 20, 30. That is, for example, both wires 20, 30 can be placed, e.g. inserted, within a coupler or other clamping member and frictionally held therein. The collar 26 has a lumen 24 extending therethrough which is configured to receive a tracking wire or guidewire 30. In this manner, a conventional guidewire can be secured to the cutting wire 20 and the connected wire assembly can be utilized as described below. As shown, the coupler 25 extends around a 360 degree arc to fully enclose the tracking wire 30 when attached. It is also contemplated that it can extend for less than 360 degrees, such as coupler 64 shown in FIG. 4B, to provide a clamp type member 65 on the tracking wire to retain the tracking wire. That is, the clamp type member 65 as shown is C-shaped with an elongated opening or channel 67 through which a tracking wire can be inserted and frictionally clamped thereto to form the cutting assembly.

It should be appreciated that although a collar is illustrated for securement of the tracking wire to the cutting wire, other ways to connect the wire are also contemplated. For example, one or more magnets may be positioned inside the collar 25 or clamp 65 to magnetically attract and retain a distal portion of the tracking wire 30. Interlocking mechanisms, snap fits etc. can also be utilized.

The cutting wire 20 remains unattached proximal of the distal connection to enable it to be separated from the tracking wire 30, e.g. moved transversely with respect to the longitudinal axis of the tracking wire 30. In FIG. 5C, the initial position of the wires 20, 30 are shown; in FIGS. 5D and 5E the wires are separated as described in detail below.

Note the tracking wire and cutting wire can be of substantially the same length, both extending out of the body for reinsertion of a catheter over the tracking wire as described below. Alternatively, they can be of different lengths.

In an alternate embodiment, multiple cutting wires can be provided with a coupler to mount/secure a tracking wire or guidewire. This is shown for example in FIG. 1A where two cutting wires 220a, 220b (additional cutting wires are also contemplated) are joined at a distal tip 223, 233, at distal regions 222, 232, respectively, by a coupler 245. Tracking wire 230 can then be inserted into coupler 245, as indicated by the arrow, forming wire assembly 210 for insertion in the same manner as wire assembly 10 discussed below. The coupler can be in the various forms described above e.g. a separate component or integral with one of the wires, and the tracking wire can be connected to the coupler in the various ways described above.

Various configurations of the cutting wire 20 are illustrated to effectively treat lesions. Such variations can also be provided in one or more of the wires 220a, 220b in the multiple wire embodiments. In the embodiment of FIGS. 1-4, the wire 20 is substantially circular in cross-section until a transition region, i.e. region 28, preferably at a distal region, where it transitions to a wire substantially triangular in cross section forming a V-shaped cutting surface 27 on a first surface opposite a second surface 29 facing the tracking wire 30. Convex surface (or alternatively a concave surface) can be formed on one, two or all three sides such as sides 70, 70b, 70c of wire 70 of FIG. 3A. A convex surface on the side opposite the cutting edge helps to conform to the outer surface of the catheter balloon. The cutting region is designated by reference numeral 21 (see FIG. 4) and can transition back to a substantially circular cross-section distal of the cutting region 21 or have such configuration extending to the coupler 25. The circular cross-section proximal and distal of the cutting region 21 provides an atraumatic wire portion.

Other cross-sectional shapes of the cutting wire 20 (and wires 220a, 220b) are contemplated, including but not limited to polygonal shapes that are substantially rectangular, square, trapezoidal (see e.g. wire 75 of FIG. 3B), hexagonal, pentagonal, octagonal, diamond shaped, etc. A round or oval wire cross-section with a sharpened surface is also contemplated. In the embodiment of FIG. 3C, a rhombus shape wire 80 in cross section is illustrated. This shape facilitates cutting if the cutting wire is rotated. FIG. 3D illustrates a caltrop shape wire 82 configured so that one point will always point upward. FIG. 3E illustrates an upside down T-shape wire 84. The base 86 can alternatively be convex.

Note, if desired, only a portion of the cutting wire 20 can have the cutting edge or surface, e.g. the distal region, with a remaining portion being atraumatic and non-cutting.

One method of use of the wire assembly 10 of the present invention will now be described. Initially, a conventional angioplasty catheter 100 is inserted over a conventional guidewire 150 to the treatment site as shown in FIG. 5. Guidewire 150 extends through a lumen 112 in the catheter 100. Access to the vessel can be obtained through the femoral artery or vein for example. Note the proximal end of the catheter 100 and guidewire 150 extend outside the patient's body. The angioplasty catheter 100 has an inflatable balloon 120 which is in fluid communication with an inflation lumen of the catheter as is conventional. At the target site, inflation of the balloon 120 expands the balloon to expand the lesion B and widen the lumen of the vessel V.

If the stenotic lesion cannot be successfully opened by a conventional balloon due to lack of force, the cutting wire of the present invention can be utilized. In this case, the guidewire 150 is removed from the guidewire lumen 112 of the catheter 100 (see FIG. 5A) and the wire assembly 10 is inserted through the lumen 112 as shown in FIG. 5B. The wire assembly 10 is formed by the user inserting the tracking guidewire 30 (or alternatively the same guidewire 150) through the lumen 24 of the collar 26 of cutting wire 20 wherein it is frictionally engaged. (The assembly can also be formed in the other ways described above.) With the wires 20, 30 secured, e.g. clamped together, they are inserted into and through the lumen 112 of the catheter, thus enabling the tracking guidewire 20 and cutting wire 30 of the created wire assembly 10 to be inserted to the target site.

Next, the catheter 100 is removed from the treatment site and vessel, and removed from the body, leaving the wire assembly 10 at the target site as shown in FIG. 5C. The catheter 100 is then reinserted over proximal end of tracking wire 30. Note that instead of reinserting the same catheter used in the step of FIG. 5, alternatively, a different balloon catheter (or catheter with other expandable member(s) such as a mechanical expander) can be inserted. In either event, the catheter 100 is inserted over the proximal portion of the tracking wire 30 such that the tracking wire 30 extends through the catheter lumen 112; however, cutting wire 20 remains outside the lumen 112 as shown in FIG. 5D. In this manner, the tracking wire 30 provides a guide for the catheter 100 to the target site, while the cutting wire 20 remains adjacent an outer surface of the catheter 100 for subsequent expansion into contact with the lesion. As shown in FIG. 5D, there is an increased gap 125 between the cutting wire 20 and tracking wire 30 caused by the catheter 100 positioned between the two wires 20, 30.

To expand or move the wire 20 transversely with respect to the longitudinal axis of the tracking wire 30 (and transverse to the longitudinal axis of the catheter 100), the balloon 120 is inflated, forcing the cutting wire 20 into contact with the lesion B so the cutting edge or surface can treat the lesion. It should be appreciated that instead of a balloon, a mechanical expander or other structure can be used to force the cutting wire 20 into contact with the lesion. If desired, the balloon 120 can be deflated and the wire assembly easily rotated to another position for subsequent transverse movement by the balloon 120 into contact with another region of the lesion B. In this manner, the select portions of the stenosis can be treated, as the cutting wire is expanding in one direction. In the multiwire embodiment of FIG. 1A, the foregoing method is the same except that expansion of the balloon forces the several wires into contact with the lesion and fewer, if any, rotations are required.

As can be appreciated, the method described above utilizes the same catheter for the initial step (FIG. 5) as well as for the subsequent step of reinsertion for placement only over the tracking wire 30 (FIG. 5D). However, it is also contemplated that a different catheter can be used for insertion over tracking wire 30 in the step of FIG. 5D.

As can be appreciated, the wire assembly 10 can accommodate balloon catheters having relatively small guidewire lumens. Also, as can be appreciated a conventional guidewire can be utilized so the user can decide the type of guidewire (tracking wire) to be used in the procedure.

Also, although access is described through the femoral artery, other approaches to the target site are also contemplated. Additionally, although described for use to treat lesions in vessel lumens, it can also be used to remove other structures constricting the passageway in the vessel or in other body lumens.

The cutting and tracking components are illustrated as wires, but other structures for the cutting member and tracking member are also contemplated such as a hard plastic tube or a metal hypotube. The metal hypotube can be formed with a cutting surface or alternatively have a cutting member such as a cutting tube attached thereto.

The cutting wire assembly of the present invention as described can be used in various vessels including for example, veins such as the femoral veins, grafts such as dialysis grafts, etc. Other vessels are also contemplated such as use in carotid arteries, coronary arteries, the descending aorta and renal arteries, the external iliac and internal iliac arteries and the common femoral and deep femoral arteries. Applications for this device include, but are not limited to, treating stenotic venous and arterial anastomosis, lesions resistant to conventional angioplasty, stent restenosis, and vessels with buildup of intima, etc.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An assembly formed by a clinician for treating a lesion in a body lumen to enlarge a passageway in the body lumen, the assembly comprising a separate cutting member and a separate tracking member initially unattached to the cutting member prior to assembly by a clinician, the tracking member configured to receive a member thereover for interposition between the cutting member and the tracking member, the cutting member having a proximal portion and a distal portion and a coupler at the distal portion for the clinician to couple the separate tracking member to the cutting member to form the assembly, the assembly having the proximal portion of the cutting member and the proximal portion of the tracking member extending outside the body when the assembly is positioned within the body adjacent the lesion and the cutting member and tracking member are separated from each other and configured for insertion of the member over the tracking member and not over the cutting member such that the tracking member is internal of the member and the cutting member is external of the member, the coupler having an opening dimensioned to receive the tracking member to retain a distal portion of the tracking member adjacent the distal portion of the cutting member when assembled by the clinician, the cutting member with coupled tracking member being insertable into the body lumen as a unit, the cutting member configured for movement by the member inserted over the tracking member in a direction transverse to a longitudinal axis of the tracking member to widen a gap between the cutting member and tracking member at least at a distal region.

2. The assembly of claim 1, wherein the cutting member has a cutting surface on a first surface opposite a second surface facing the tracking member.

3. The assembly of claim 2, wherein the second surface has a convex surface.

4. The assembly of claim 1, wherein the tracking member and cutting member are each in the form of a wire and the coupler includes a collar at the distal portion of the cutting member.

5. The assembly of claim 4, wherein the tracking member is frictionally engaged within the opening of the coupler.

6. The assembly of claim 1, wherein the cutting member is in the form of a wire and the tracking member is in the form of a wire.

7. The assembly of claim 6, wherein the cutting member has a cutting surface on a first surface opposite a second surface facing the tracking member, and transverse movement of the cutting member moves the cutting surface into contact with the lesion.

8. The assembly of claim 1, wherein a length of the tracking member exceeds a length of the cutting member.

9. The assembly of claim 1, wherein the cutting member has a first elongated portion of a first cross-sectional configuration and a second elongated portion of a second different cross-sectional configuration, the second elongated portion including a cutting surface and the first elongated portion being proximal of the second elongated portion and being atraumatic.

10. The assembly of claim 1, wherein the coupler is a separate component from the cutting member.

11. The assembly of claim 1, wherein the coupler is integral with the cutting member.

12. The assembly of claim 1, further comprising a second cutting member coupled to the coupler and configured for movement in a direction transverse to the longitudinal axis of the tracking member to widen a gap between the second cutting member and tracking member.

13. A cutting assembly for treating a lesion in a body lumen of a patient to enlarge a passageway in the body lumen, the assembly comprising at least one cutting member having a proximal portion and a distal portion, a separate unattached tracking member, and a coupler for coupling the separate unattached tracking member to the at least one cutting member by a clinician to form the cutting assembly, the coupler positioned at a distal portion of the cutting member and including an opening dimensioned to receive the tracking member, the at least one cutting member having a cutting surface engageable with the lesion, the tracking member configured to receive a member thereover for interposition between the cutting member and the tracking member, the cutting assembly being insertable into the body lumen and advanceable to a region adjacent the lesion, the at least one cutting member having a free end at a proximal portion and the free end extending outside the patient when the assembly is positioned adjacent the lesion, the at least one cutting member configured by application of a radial force by the member inserted over the tracking member, wherein the cutting member remains external of the member, for movement of the at least one cutting member in a direction transverse to the tracking member to widen a gap between the at least one cutting member and the tracking member at least at a distal region so the cutting surface of the at least one cutting member applies a cutting action to the lesion.

14. The assembly of claim 13, wherein the coupler is attached to a distal portion of the tracking member.

15. The assembly of claim 13, wherein the cutting surface is positioned on a distal region of the at least one cutting member and other proximal portions which are proximal of the cutting surface of the at least one cutting member are atraumatic.

16. The assembly of claim 13, wherein the at least one cutting member is in the form of a wire.

17. The assembly of claim 13, wherein the tracking member is in the form of a guidewire.

18. The assembly of claim 13, wherein the at least one cutting member includes two cutting members movable in different directions with respect to the tracking member.

19. The assembly of claim 13, wherein the cutting member has a first elongated portion and a second elongated portion, the second elongated portion including a cutting surface and the first elongated portion being proximal of the second elongated portion and being atraumatic.

* * * * *